United States Patent
Kim et al.

(10) Patent No.: US 10,189,875 B2
(45) Date of Patent: Jan. 29, 2019

(54) ANTI-CANCER PEPTIDE AND USE THEREOF

(71) Applicant: ENSOL BIOSCIENCES INC., Daejeon (KR)

(72) Inventors: Hae Jin Kim, Daejeon (KR); Duk Soon Hwang, Daejeon (KR); Eun Joung Moon, Gyeongsan-si (KR)

(73) Assignee: ENSOL BIOSCIENCES INC., Daejeon (KR)

( * ) Notice: Subject to any disclaimer, the term of this patent is extended or adjusted under 35 U.S.C. 154(b) by 0 days.

(21) Appl. No.: 15/741,150

(22) PCT Filed: Jul. 22, 2016

(86) PCT No.: PCT/KR2016/008062
§ 371 (c)(1),
(2) Date: Dec. 29, 2017

(87) PCT Pub. No.: WO2017/014604
PCT Pub. Date: Jan. 26, 2017

(65) Prior Publication Data
US 2018/0186834 A1    Jul. 5, 2018

(30) Foreign Application Priority Data
Jul. 23, 2015    (KR) .................. 10-2015-0104332

(51) Int. Cl.
| A61K 38/08 | (2006.01) |
| A61K 38/00 | (2006.01) |
| C07K 7/06 | (2006.01) |
| C07K 7/00 | (2006.01) |
| A61P 35/04 | (2006.01) |

(52) U.S. Cl.
CPC ............... C07K 7/06 (2013.01); A61P 35/04 (2018.01); A61K 38/00 (2013.01); A61K 38/08 (2013.01)

(58) Field of Classification Search
CPC .......... A61K 38/08; A61K 38/00; C07K 7/06; C07K 7/00
USPC ......... 514/21.8, 19.2, 19.3, 19.4, 19.5, 19.6, 514/19.8; 530/330
See application file for complete search history.

(56) References Cited

U.S. PATENT DOCUMENTS

| 5,595,756 A * | 1/1997 | Bally .................. A61K 9/1272 264/4.1 |
| 2003/0017170 A1 | 1/2003 | Fukuda |
| 2007/0178533 A1* | 8/2007 | Poccia ................. G01N 33/505 435/7.2 |
| 2013/0302343 A1* | 11/2013 | Becher .................. C07K 16/18 424/142.1 |

FOREIGN PATENT DOCUMENTS

| EP | 0397635 A1 | 11/1990 |
| JP | 2014-065680 A | 4/2014 |
| JP | 2015-510393 A | 4/2015 |
| KR | 10-2011-0044374 A | 4/2011 |
| KR | 10-2013-0099131 A | 9/2013 |
| KR | 10-2014-0118271 A | 10/2014 |
| KR | 10-2014-0123311 A | 10/2014 |
| WO | 2006084016 A1 | 8/2006 |
| WO | 2007/133033 A1 | 11/2007 |
| WO | 2012002668 A2 | 1/2012 |

OTHER PUBLICATIONS

UniProt D0E4I0, pp. 1-2. Integrated into UniProtKB/TrEMBL on Nov. 24, 2009.*
Neidle, Stephen, ed., Cancer Drug Design and Discovery, Elsevier/Acadmic Press, pp. 427-431, 2008.*
Gura T, "Systems for Identifying new Drugs Are Often Faulty," Science, Nov. 7, 1997, 278: 1041-1042.*
Jain RK, "Barriers to Drug Delivery in Solid Tumors," Scientific American, Jul. 1994, 58-65.*
Sporn MB, "Chennoprevention of cancer," Carcinogenesis, 2000, 21(3): 525-530.*
Gravanis I, "The changing wrold of cancer drug development: the regulatory bodies' perspecctive," Chinese Clinical Oncology, 2014, 3(2): 1-5.*
Hait WN, "Anticacner drug development: the grand challenges," Nature Reviews, Apr. 2010, 9: 253-254.*
Lik Tong Tan, Filamentous tropical marine cyanobacteria: a rich source of natural products for anticancer drug discovery, J Appl Phycol, Oct. 27, 2009, pp. 659-676.
Matthew J. Betts et al., Amino Acid Properties and Consequences of Substitutions, Bioinformatics for Geneticists, Jan. 1, 2003, pp. 289-316.

* cited by examiner

*Primary Examiner* — Julie Ha
(74) *Attorney, Agent, or Firm* — Novick, Kim & Lee, PLLC; Jae Youn Kim

(57) ABSTRACT

Provided are a peptide consisting of the amino acid sequence of SEQ ID NO:1 or a pharmaceutically acceptable salt thereof, and the use thereof. Cancer can be effectively prevented or treated by application of the peptide.

11 Claims, 2 Drawing Sheets

Specification includes a Sequence Listing.

ANTI-CANCER PEPTIDE AND USE THEREOF

CROSS-REFERENCE TO RELATED APPLICATIONS

The instant application is a U.S. national-stage application under 35 USC § 371 of PCT application number PCT/KR2016/008062 filed on Jul. 22, 2016, and claims priority under 35 USC § 119 to Korean patent application number 10-2015-0104332, filed on Jul. 23, 2015.

TECHNICAL FIELD

The present invention relates to a novel peptide and, more particularly, to a novel peptide and use thereof.

BACKGROUND ART

Cancers (or tumors) result from the uncontrollable proliferation of cells in living tissues. Cancer cells invade surrounding tissues or spread to other organs, often leading to death.

Methods of treating such cancer include surgery, radiation therapy, chemotherapy, immunotherapy, etc., and research into peptides that exhibit anticancer effects is ongoing (International Patent Application Publication No. WO 2007/133033 A1).

CITATION LIST

Patent Literature (Patent Document 1) International Patent Application Publication No. WO 2007/133033 A1, Nov. 22, 2007, Abstract

DISCLOSURE OF INVENTION

Technical Problem

Accordingly, the present invention has been made keeping in mind the above problems occurring in the related art, and the present invention is intended to provide a novel peptide.

In addition, the present invention is intended to provide novel use of the peptide.

Additional technical problems, which are not mentioned in the foregoing, will be readily understood by those skilled in the art from the following description.

Solution to Problem

The present invention provides a peptide consisting of an amino acid sequence (QLHLD) of SEQ ID NO:1, or a pharmaceutically acceptable salt thereof.

In the amino acid sequence, Q designates glutamine (Gln), L designates leucine (Leu), H designates histidine (His), and D designates aspartate (Asp).

The amino acids that constitute the peptide include L-, D-, and DL-forms, all of which are incorporated in the present invention. Furthermore, it will be apparent that Asp may be interpreted as having a meaning including aspartic acid, as well as aspartate, as the amino acid.

The peptide includes variants thereof in which a portion of the peptide structure according to the present invention is varied by natural mutation or artificial mutation without changing the main activity thereof.

Examples of the pharmaceutically acceptable salt may include hydrochloride, sulfate, phosphate, acetate, citrate, tartrate, succinate, lactate, maleate, fumarate, oxalate, methane sulfonate, and para-toluene sulfonate.

In addition, the present invention provides medical use of the peptide according to the present invention or the pharmaceutically acceptable salt thereof, preferably for anticancer use, and more preferably for the prevention or treatment of cancer. Here, the term "treatment" comprehensively means the reduction or alleviation of symptoms associated with cancer, and the term "prevention" is used as the comprehensive meaning including inhibition of progression of the disease from the asymptomatic stage before disease.

The cancer may be metastatic cancer.

In the present invention, an anticancer effect may be exhibited by inhibiting at least one selected from among invasion and metastasis of cancer cells.

Accordingly, the present invention provides an anticancer composition comprising the peptide of the present invention or the pharmaceutically acceptable salt thereof. Additionally, the present invention provides a composition for use in the treatment or prevention of cancer, comprising the peptide of the present invention or the pharmaceutically acceptable salt thereof. The treatment or prevention of cancer may be achieved by inhibiting at least one selected from among invasion and metastasis of cancer cells. The composition may be a pharmaceutical composition.

The pharmaceutical composition contains, as an active ingredient, the peptide according to the present invention or the pharmaceutically acceptable salt thereof.

Also, the pharmaceutical composition further includes a pharmaceutically acceptable additive, and may thus be composed of the peptide according to the present invention or the pharmaceutically acceptable salt thereof and the additive.

The peptide according to the present invention may be prepared by methods typically useful in the field of peptide chemistry. For example, the peptide may be prepared by the method disclosed by Schroder and Lubke, [The Peptides] Vol. 1, Academic Press, New York (1965), or by the method such as solution synthesis or solid synthesis.

Examples of the process for forming a peptide bond may include an acyl azide method, an acyl halide method, an acyl imidazole method, a carbodiimide method, a phosphonium method, an anhydride method, a mixed anhydride method, an oxidation-reduction method, and the use of Woodward's reagent K.

Before the condensing reaction, a carboxyl group, an amino group or the like, which does not participate in the reaction, may be protected, and a carboxyl group that participates in the condensing reaction may be activated by methods known in the art.

Examples of the functional group for protecting the carboxyl group may include ester-forming groups, such as methyl, tert-butyl, aryl, pentafluorophenyl, benzyl, paramethoxybenzyl, and methoxyethoxymethyl.

Examples of the functional group for protecting the amino group may include trityl carbonyl, aryloxycarbonyl, cyclohexyloxycarbonyl, trichloroethyloxycarbonyl, benzy-loxycarbonyl, tert-butoxycarbonyl, and/or 9-fluorenylmethyloxycarbonyl.

Examples of the active form of the carboxyl group may include mixed anhydride, azide, acyl chloride, and active ester [ester with alcohol (e.g. pentachlorophenol, 2,4-dinitrophenol, cyanomethyl alcohol, p-nitrophenol, N-hydroxy- 5-norbornene-2,3-dicarboxylimide, N-hydroxysuccinimide, N-hydroxyphthalamide, or 1-hydroxybenzotriazole)].

The solvent usable in the condensing reaction for forming a peptide bond may include benzene, toluene, hexane, acetone, nitromethane, cyclohexane, ether, chloroform, dichloromethane, ethylacetate, N,N-dimethylformamide, dimethylsulfoxide, pyridine, dioxane, tetrahydrofuran, water, methanol, and ethanol, which may be used alone or in combination.

The reaction temperature ranges from about −70 to 100° C., and preferably from −30 to 30° C.

The deprotection reaction for removing the protecting group from the peptide may be carried out using an acid compound, a base compound, or a transition metal, capable of removing the protecting group without influencing the peptide bond, depending on the kind of protecting group.

The deprotection reaction may be performed through acid treatment using, for example, hydrogen chloride, hydrogen bromide, hydrogen fluoride, acetic acid, methanesulfonic acid, trifluoromethanesulfonic acid, trifluoroacetic acid, trimethylchlorosilane, or mixtures thereof.

When the deprotection reaction is carried out through acid treatment, it may be promoted by the addition of an adjuvant such as anisole, phenol or thioanisole.

Alternatively, the deprotection reaction may be performed through base treatment using, for example, ammonia, diethylamine, hydrazine, morpholine, N-methylpyrrolidine, piperidine, sodium carbonate, or mixtures thereof.

Alternatively, the deprotection reaction may be performed through transition metal treatment using, for example, zinc, mercury, palladium/hydrogen, etc.

After completion of the reaction, the peptide may be purified using a typical purification process, such as extraction, layer separation, solid precipitation, recrystallization, or column chromatography.

Moreover, the peptide according to the present invention may be converted into a variant thereof or a pharmaceutically acceptable salt thereof using a typical process.

The peptide according to the present invention may be synthesized using an automatic peptide synthesizer, or may be produced through genetic engineering. For example, a fusion gene encoding a fusion protein comprising a fusion partner and the peptide according to the present invention is produced through genetic engineering, and is then used to transform a host microorganism, whereby the fusion protein is expressed in the host microorganism, after which the peptide according to the present invention is cleaved or separated from the fusion protein using a proteolytic enzyme or compound, thus yielding a desired peptide.

The peptide or the pharmaceutically acceptable salt thereof is parenterally administered in an amount of 200 to 500 mg/day, and preferably 267 to 400 mg/day. The administered peptide or the pharmaceutically acceptable salt thereof may be for an adult (about 60 kg). Upon oral administration, the amount thereof corresponds to 2 to 5 times the amount upon parenteral administration. The peptide according to the present invention may be mainly administered through parenteral routes, for example, topical injection, intravenous or subcutaneous injection, intracerebral or intraspinal administration, or nasal or intrarectal administration. In some cases, oral administration is possible.

The peptide or the composition according to the present invention may be formulated in the form of an injection, a suppository, a powder, a nose drop, a granule, or a tablet, together with a pharmaceutically acceptable additive.

The pharmaceutically acceptable additive may be applied depending on a variety of factors well-known to those skilled in the art, including, for example, a specific bioactive material, its concentration, stability and intended bioavailability; disorders and diseases to be treated or conditions associated therewith; individuals to be treated, their age, size, and general health status; and composition administration routes, for example, nasal, oral, ocular, topical, dermal and muscle routes, but the present invention is not limited thereto. The pharmaceutically acceptable additive, which is used for administration of the bioactive material, in addition to the oral administration route, may include an aqueous solution including D5W (5% glucose in water), dextrose and a physiological salt in an amount within 5% of the volume thereof. For topical intralesional injection, any injectable hydrogel may be used to enhance therapeutic effects and increase the duration. The pharmaceutically acceptable additive may contain additional components for improving the stability of active components such as preservatives and antioxidants. The peptide or the composition according to the present invention may be produced through appropriate methods in the related field, and for example, is preferably formulated so as to be suitable for each disease or component by the method disclosed in Remington's Pharmaceutical Science, Mack Publishing Company, Easton Pa. (latest).

The peptide of the present invention may be stored in a saline solution, or may be lyophilized in an ampoule after the addition of mannitol or sorbitol and may be administered after dissolution in saline.

In addition, the present invention provides a method of treating or preventing cancer, including administering the peptide or the pharmaceutically acceptable salt thereof of the present invention to mammals, including humans, in need of administration. In addition, the present invention provides use of the peptide or the pharmaceutically acceptable salt thereof of the present invention in the manufacture of an anticancer medicament, and preferably in the manufacture of a medicament for use in the treatment or prevention of cancer. The treatment or prevention of cancer may be achieved by inhibiting at least one selected from among invasion and metastasis of cancer cells. The administered peptide or pharmaceutically acceptable salt thereof may be a peptide or pharmaceutically acceptable salt thereof in an effective amount.

Unless otherwise mentioned, the matters described in connection with the peptide or pharmaceutically acceptable salt thereof, the use, the composition, and the method according to the present invention are applicable to each other under the scope of identity as far as they are not contrary to each other.

Advantageous Effects of Invention

According to the present invention, cancer can be effectively treated or prevented.

MODE FOR THE INVENTION

Figure 1:
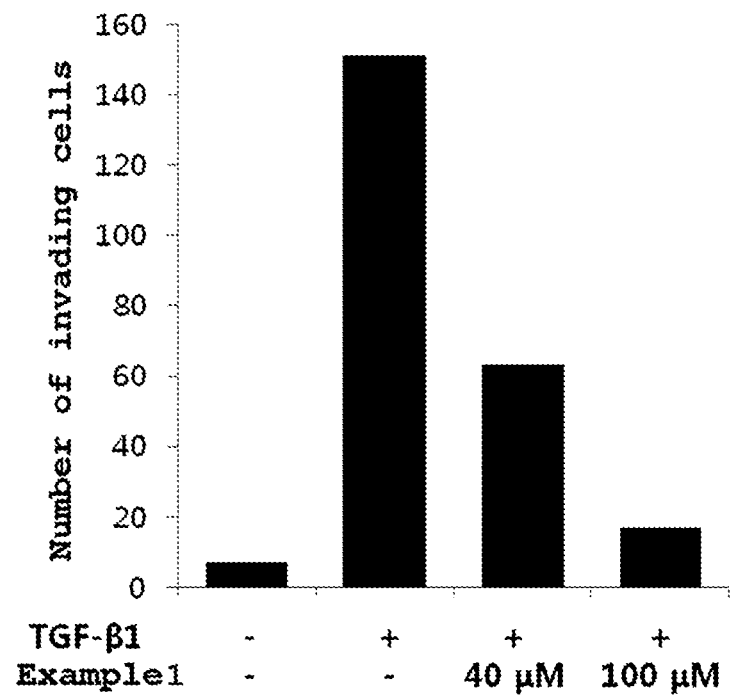
FIG. 1 is a graph illustrating the effects of an embodiment of the present invention on the invasion of cancer cells.

A better understanding of the present invention is given through the following examples and preparation example, which are merely set forth to illustrate but are not to be construed as limiting the present invention.

The term "anticancer" refers to the ability to treat or prevent cancer, and particularly an anticancer effect may be exhibited by inhibiting at least one selected from among the invasion and metastasis of cancer cells.

The reagents used in the Examples below are commercially available and best products, and are purchased from Sigma-Aldrich, unless otherwise mentioned.

<Example 1> Preparation of Peptide

A peptide (QLHLD: SEQ ID NO:1) consisting of the amino acid sequence of SEQ ID NO:1 was prepared by AnyGen Co., Ltd., Korea. Specifically, it was synthesized by a solid phase method using the chemical properties of Fmoc (9-fluorenylmethoxycarbonyl). More specifically, a C-terminal of the peptide was coupled with 0.55 mmol/g of a solid resin (Wang resin; Sigma-Aldrich). The coupling of Fmoc-Phe-OH amino acid was carried out together with 0-benzotriazoleN,N,N',N'-tetramethyl-uronium-hexafluorophosphate (HBTU). The amino acid side-chain was protected by tert-butyl and tert-butyloxycarbonyl. Deprotection and resin separation were performed at room temperature for 3 hr using a mixed solution comprising trifluoroacetic acid and water at a ratio of 95:5 (v/v). A crude peptide was repeatedly washed with diethylether, dried in a vacuum, and then purified via reverse-phase high-performance liquid chromatography (RP-HPLC) using a Shimadzu 5 gm Shimpak ODS C18 column (20×250 mm). The purified peptide was identified via analytical RP-HPLC using a Shimpak 5ftm ODS C18 column (4.6×250 mm). The molecular weight of the synthesized peptide was measured using a matrix-assisted laser desorption ionization (MALDI)-mass spectrometer (Axima CFR, Kratos Analytical, Manchester, UK).

<Example 2> Evaluation of Inhibitory Effect on the Invasion of Cancer Cells

Whether the invasion of cancer cells was inhibited by the peptide of Example 1 was evaluated experimentally. Specifically, in order to evaluate the effect of the peptide of Example 1 on inhibiting the invasion of cancer cells, a Transwell invasion assay was performed. Growth factor reduced Matrigel (BD Biosciences, Franklin Lakes, N.J., USA) was diluted at 1:1 with a medium [RPMI 1640 medium (Welgene Inc., Korea)] and 70 fek thereof was added to the top chamber of the Transwell insert (Corning cat#3422, Tewksbury Mass., USA), followed by a coating process for 1 hr in a $CO_2$ incubator at 37° C. 500 fek of a medium [RPMI 1640 medium (Welgene Inc., Korea)] containing 10% fetal bovine serum (FBS, Cellgro cat#35-015-CV, USA) was added to the bottom chamber, after which the test group was added with 10 ng/ml of TGF-beta1 (PromoKine, Germany). The coated top chamber was mounted to the bottom chamber, and 100 ick of RPMI 1640 medium containing 0.5% FBS with 20000 SNU-790 thyroid cancer cells (Korean Cell Line Bank) was added to the top chamber. In this way, a negative control group and two test groups were prepared. Respective test groups were treated with the peptide of Example 1 in amounts of 40 [1M and 100 [1M, and the negative control group was not treated with the peptide of Example 1. Also, a control group was prepared in the same manner as the negative control group, with the exception that TGFbeta1 (Transforming growth factor beta1) was not added.

The test groups, the control group, and the negative control group were cultured in a $CO_2$ incubator for 2 days at 37° C. After completion of the culture, the cells remaining in the top chamber were completely removed using a cotton swab. The cells, which were attached to the outer surface of the top chamber, were washed with DPBS (Dulbeco's Phosphate-Buffered Saline) for 5 min, fixed in 100% methanol at −20° C. for 5 min, and then stained for 15 min with a Mayer's Hematoxylin solution (Sigma-Aldrich), followed by washing with tap water for 5 min, fixing in 100% ethanol for 5 min, and then staining for 15 min with eosin Y solution. Finally, washing with 100% ethanol was performed, and the membrane to which the cells were attached was cut by a blade, placed on a slide glass and observed with a microscope. Four randomly selected regions were photographed and the number of cells in these regions was counted, averaged and graphed. FIG. 1 is a graph showing the above results, plotted with the x-axis for each group and the y-axis for the number of invading cells. As shown in FIG. 1, the invasion of cancer cells, which was increased by TGF-beta 1, was inhibited in a concentration-dependent manner by the peptide of Example 1.

Therefore, the peptide according to the present invention was effective at inhibiting the invasion of cancer cells, thereby exhibiting anticancer effects.

Figure 2:
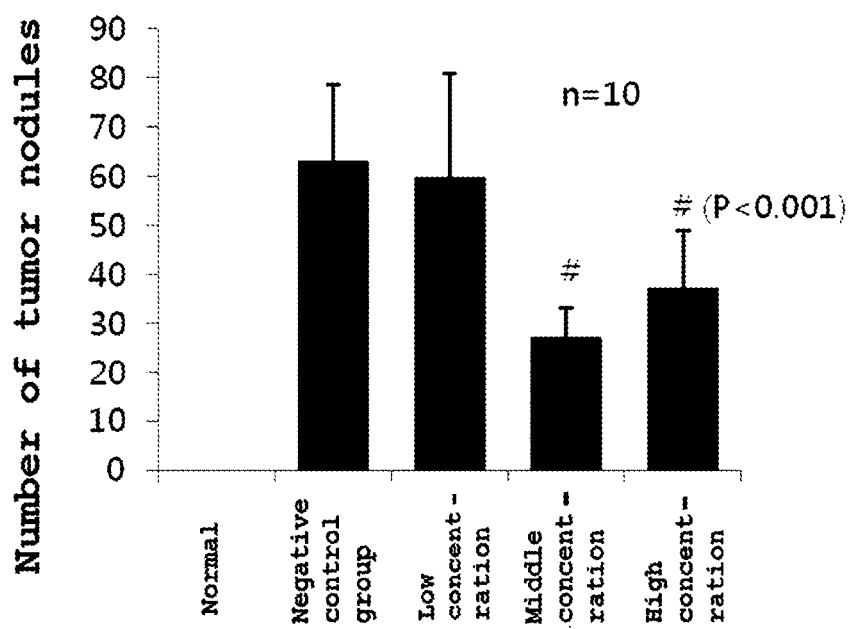
FIG. 2 is a graph illustrating the effects of an embodiment of the present invention on the metastasis of cancer cells.

<Example 3> Evaluation of Inhibitory Effect on Metastasis of Cancer Cells In Vivo Whether the metastasis of cancer cells was inhibited by the peptide of Example 1 was evaluated experimentally. Specifically, in order to evaluate the inhibitory effect of the peptide of Example 1 on the metastasis of cancer cells, testing was performed using a lung metastasis model with 4T1 mouse breast cancer cells (ATCC CRL-2539, USA). The peptide of Example 1 was injected into the caudal vein of the tail of female BALB/c mice (SPF, SLC/Japan). The test group was divided into three groups according to the administration concentration; low concentration [40/2 g/head], middle concentration [80/2 g/head], and high concentration 1120, ug/headl. The negative control group was treated in the same manner as the test group, with the exception that the peptide of Example 1 was not administered. On the day after first administration, 4T1 cells (1.5× $10^4$ cells/head) were injected into the mouse tail caudal vein. After 1 hr, the peptide of Example 1 was secondarily administered. The administration of the peptide was performed three times a week (Monday, Wednesday, and Friday) for a total of three weeks ranging from the second administration day to the final administration day. The weight of the mouse was measured two times a week, and an autopsy was performed on the 21st day after the injection of cancer cells. The lung tissue was excised, stained with a Bouin's solution, and fixed, and then the number of metastatic tumor nodules was counted. Also, a group (a normal group), treated in the same manner as the test group, was prepared as a control group, with the exception that neither the peptide of Example 1 nor 4T1 cells were added. The results are shown in FIG. 2. The graph of FIG. 2 is plotted with an x-axis for each group and a y-axis for the number of tumor nodules. As such, n designates the number of individuals in each group, and P designates the significance probability. As illustrated in FIG. 2, in the test groups in which the peptide of Example 1 was administered at middle concentration and high concentration, the number of tumor nodules was significantly ($P<0.001$) reduced. In particular, the inhibitory effect of cancer metastasis was the highest in the test group in which the peptide was administered at the middle concentration.

Therefore, the peptide of the present invention is effective at inhibiting the metastasis of cancer cells, thereby exhibiting anticancer effects.

<Example 4> Evaluation of Anticancer Effect I

The anticancer effect of the peptide of Example 1 was evaluated experimentally. Specifically, in order to evaluate the effect of the peptide of Example 1 on surviving individuals suffering from cancer, the survival rate was measured using an animal model prepared in the same manner as in Example 3.

Figure 3:
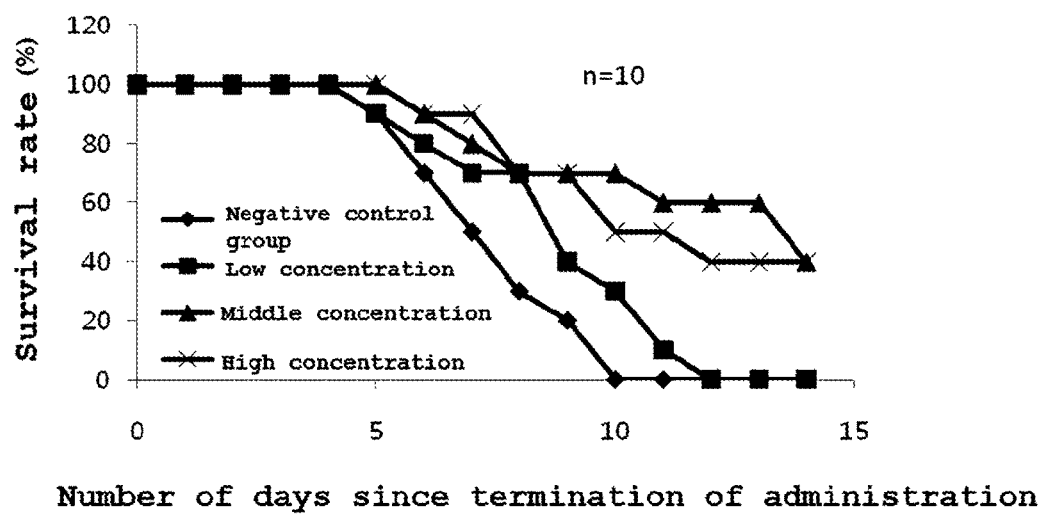
FIGS. 3 and 4 are graphs illustrating the anticancer effects according to an embodiment of the present invention.

The negative control group and the test group were prepared in the same manner as in Example 3, except for the autopsy and subsequent treatment. To measure the survival rate, the survival rate for each group was observed and recorded. The results are shown in FIG. 3. In the graph of FIG. 3, showing the survival rate, the x-axis represents the number of days since termination of administration, and the y-axis represents the survival rate (%). Also, n represents the number of individuals in each group. As illustrated in FIG. 3, in the test groups in which the peptide of Example 1 was administered at middle and high concentrations, some individuals survived even after the death of the negative control group. In particular, the survival rate was the highest in the test group in which the peptide was administered at the middle concentration.

Therefore, the peptide of the present invention can be found to exhibit anticancer effects.

<Example 5> Evaluation of Anticancer Effect II

The anticancer effect of the peptide of Example 1 was evaluated experimentally. Specifically, in order to evaluate the effect of the peptide of Example 1 on surviving individuals suffering from cancer, the survival rate was measured using an animal model with B16-BL6 mouse melanoma cells (Korean Cell Line Bank, Korea).

Figure 4:
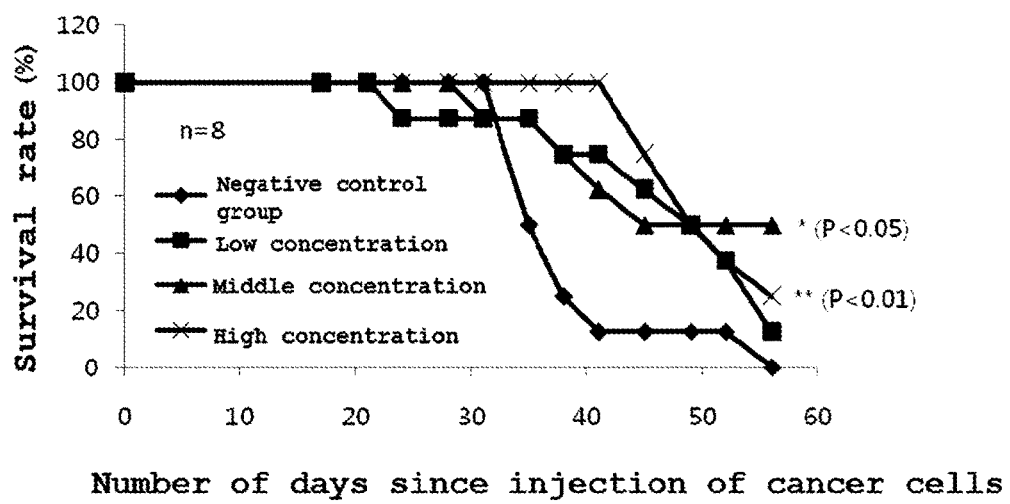

B16-BL6 cells {$1 \times 10^5$ cells/head} were subcutaneously injected into 7-week-old male C57BL/6J mice (Orientbio Inc., Korea). After one week, the peptide of Example 1 was intraperitoneally administered. The test group was divided into three groups according to the administration concentration; low concentration {40, ttg/head}, middle concentration {80, ttg/head}, and high concentration {120, ttg/head}. The negative control group was treated in the same manner as the test group, with the exception that the peptide of Example 1 was not administered. The administration was repeated two times a week for two weeks from the first administration day and then once a week for an additional four weeks, and the peptide was administered a total of eight times. To measure the survival rate, the survival rate for each group was observed and recorded. The results are shown in FIG. 4. In the graph of FIG. 4, showing the survival rate, the x-axis represents the number of days since injection of the cancer cells, and the y-axis represents the survival rate (%). Also, n represents the number of individuals in each group and P represents the significance probability. As illustrated in FIG. 4, in the test groups in which the peptide of Example 1 was administered, some individuals survived even after the death of the negative control group. In particular, the survival rate was the highest in the test group in which the peptide was administered at the middle concentration.

Consequently, the peptide according to the present invention can be found to exhibit anticancer effects.

<Preparation Example 1> Preparation of a Dosage Form for Injection 500 mg of the peptide prepared in the same manner as in Example 1 was dissolved in saline to make 10 ml of a solution. This solution was charged in an ampoule for an injection, yielding a dosage form for injection.

INDUSTRIAL APPLICABILITY

The present invention enables the effective treatment or prevention of cancer, and is thus industrially applicable.

The invention claimed is:

1. A peptide consisting of the amino acid sequence of SEQ ID NO: 1 or a pharmaceutically acceptable salt thereof.

2. A pharmaceutical composition for use in treatment of cancer, comprising the peptide of claim 1 or the pharmaceutically acceptable salt thereof, wherein the cancer is selected from the group consisting of thyroid cancer, melanoma and breast cancer.

3. The pharmaceutical composition according to claim 2, wherein the treatment of cancer is achieved by inhibiting at least one selected from among invasion and metastasis of cancer cells.

4. The pharmaceutical composition according to claim 2, wherein the cancer is thyroid cancer.

5. The pharmaceutical composition according to claim 2, wherein the cancer is melanoma.

6. The pharmaceutical composition according to claim 2, wherein the cancer is breast cancer.

7. A method of treating cancer, comprising administering an effective amount of the pharmaceutical composition according to claim 2 to a patient in need thereof, wherein the cancer is selected from the group consisting of thyroid cancer, melanoma and breast cancer.

8. The method according to claim 7, wherein the treatment of cancer is achieved by inhibiting at least one selected from among invasion and metastasis of cancer cells.

9. The method according to claim 7, wherein the cancer is thyroid cancer.

10. The method according to claim 7, wherein the cancer is melanoma.

11. The method according to claim 7, wherein the cancer is breast cancer.

* * * * *

SEQUENCE LISTING

```
<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<223> OTHER INFORMATION: peptide

<400> SEQUENCE: 1

Gln Leu His Leu Asp
 1               5
```